(12) United States Patent
Müller et al.

(10) Patent No.: US 6,452,997 B1
(45) Date of Patent: Sep. 17, 2002

(54) METHOD FOR USE IN TOMOGRAPHIC IMAGING

(75) Inventors: Timo Müller, Espoo; Mikko Jarva, Helsinki, both of (FI)

(73) Assignee: Planmeca Oy, Helsinki (FI)

( * ) Notice: Subject to any disclaimer, the term of this patent is extended or adjusted under 35 U.S.C. 154(b) by 0 days.

(21) Appl. No.: 09/700,861

(22) PCT Filed: Jun. 23, 1999

(86) PCT No.: PCT/FI99/00555

§ 371 (c)(1),
(2), (4) Date: Nov. 21, 2000

(87) PCT Pub. No.: WO00/00087

PCT Pub. Date: Jan. 6, 2000

(30) Foreign Application Priority Data

Jun. 26, 1998 (FI) ................................................. 981477

(51) Int. Cl.[7] ................................................. A61B 6/00
(52) U.S. Cl. .............................................. 378/17; 378/4
(58) Field of Search ................................. 378/17, 4, 38, 378/39

(56) References Cited

U.S. PATENT DOCUMENTS

| 4,683,581 | A | | 7/1987 | Tammisalo et al. |
|---|---|---|---|---|
| 5,086,447 | A | | 2/1992 | Siczek et al. |
| 5,345,381 | A | | 9/1994 | Wallschlaeger |
| 5,666,392 | A | | 9/1997 | Ploetz |
| 6,055,292 | A | * | 4/2000 | Zeller et al. ................... 378/21 |
| 6,118,842 | A | * | 9/2000 | Arai et al. ..................... 378/39 |
| 6,173,035 | B1 | * | 1/2001 | Tachibana et al. ............ 378/39 |

FOREIGN PATENT DOCUMENTS

| FI | 88671 | 3/1993 |
|---|---|---|
| FI | 931947 | 4/1993 |
| FI | 951282 | 3/1995 |

* cited by examiner

Primary Examiner—Robert H. Kim
Assistant Examiner—Irakli Kiknadze
(74) Attorney, Agent, or Firm—Nixon & Vanderhye P.C.

(57) ABSTRACT

This invention relates to tomographic imaging, and particularly to producing complex motion or spiral tomography images in medical X-ray imaging. According to the invention, a curved path is arranged for the radiation source of the imaging apparatus in the vertical direction with respect to the object to be imaged, and a counter-movement with respect to the curved movement of the radiation source in the vertical is implemented by moving the radiation detector substantially linearly with respect to the radiation source on the opposite side of the object to be imaged. It is also preferable to keep the detector constantly parallel with a cross-sectional plan through the object to be imaged.

24 Claims, 4 Drawing Sheets

METHOD FOR USE IN TOMOGRAPHIC IMAGING

This invention relates to a method, apparatus and their use for tomographic imaging, particularly for producing complex motion or spiral tomography images in medical x-ray imaging according to the preambles of the appended independent claims.

BACKGROUND

Imaging methods utilizing electromagnetic radiation can be divided into two groups: radioscopic methods and tomographic methods. In traditional radioscopy the radiation source, the object to be imaged and the radiation detector, e.g. an x-ray film, are stationary with respect to one another during the imaging session. Imaging methods in which a narrow beam is moved over the object to be imaged are also known.

Tomographic methods can be divided into linear (i.e. planar) tomographic methods and complex motion or spiral tomography methods. In tomographic imaging the object to be imaged and/or the radiation detector are moved with respect to each other in a controlled manner, and thus in linear tomography the tomographic movement occurs with respect to one axis and in complex motion tomography with respect to two axes. These methods use a beam which is of the same size as the object to be imaged, and the object is usually held in place as the radiation source and radiation detector are moved dependently on each other on the opposite sides of the object to be imaged in the opposite directions so that the beam penetrates the object from different directions, but its centre of movement/rotation in the object does not move. The methods provide accurate images of the imaging area in the centre of rotation of the beam, whereas the other parts of the object are blurred partially or totally.

There are also 'narrow beam tomography' methods in which a beam considerably narrower than the object to be imaged sweeps across the area to be imaged and the beam is turned with respect to the object to be imaged. In that case the imaging means (radiation source and radiation detector) must be moved in a controlled manner so that the detector moves in relation to the beam at a lateral velocity which corresponds to the perpendicular sweeping speed of the beam in the area to be imaged multiplied by the ratio of magnification, i.e. by a coefficient which is the ratio of the distance of the beam focus (=radiation source) and the distance of the focus from the area to be imaged. Here the term detector refers to a film or the like; in digital imaging, for example, the movement of the detector with respect to the area to be imaged may be replaced with a suitable electrical function, such as charge transfer on the surface of a semiconductor sensor.

Thus it is known to use both horizontal and vertical movement of the imaging means for producing a tomographic effect. Many prior art devices that enable complex motion paths have very large structures, and thus it may not be possible to move the imaging means rapidly and change their direction due to the limits set by the general physical principles of moving heavy masses and mechanical solutions of the devices. Against this background it is not easy to develop commercially feasible devices.

The present trend is to develop solutions which allow to use the same device for various purposes, i.e. the goal is to be able to use the same device in different tomographic methods and for imaging different projections. When the same device has different imaging modes, investment in imaging sensors based on modern digital technology becomes more profitable, which lowers the threshold of introducing them. Digital technology facilitates the doctors' work, for example, since it does not only allow the doctors to produce better images than earlier and thus to make more accurate diagnoses, but also to store the images and manage them in electronic form, together with all other documents related to the patient.

One prior art tomographic imaging device, which has relatively many different imaging modes, is disclosed in Finnish Patent 88671. In one embodiment according to the publication the imaging means of the device are attached to the ends of a suspension arm that can be rotated horizontally, the arm being provided with a degree of freedom for moving in the direction of the axis between the imaging means. Furthermore, the arm can be tilted with respect to the horizontal plane. According to the publication, the imaging means can also be arranged so that they can be moved vertically with respect to the object to be imaged by forming the suspension arm in the shape of an arc and by moving the arm in the direction of its longitudinal axis along a supporting structure in which the imaging means move upwards along a curved path of the arm and correspondingly downwards on the opposite sides of the object to be imaged.

The solution according to the publication utilizes a narrow beam, and the imaging means are moved vertically with respect to the object to be imaged in order to obtain a perpendicular cross-sectional image of the patient's teeth which are diagonal to the vertical plane. Thus the publication does not disclose use of the solutions described therein (which is known per se from other contexts) for actual complex motion or spiral tomography imaging, i.e. the use of the movements the structures in question enable for producing a tomographic effect with respect to two axes during radiation. On the other hand, the use of the solutions disclosed in the publication for complex motion tomographic imaging as such is somewhat problematic, because the quality of the image has to be compromised. As a result of the fact that the detector is moved along a curved path with respect to the object to be imaged by keeping it all the time perpendicular to the radiation source, i.e. parallel with the tangent of the path, the shear plane to be projected onto the detector changes constantly in the object to be imaged. Naturally, the resolution of the image produced in this way is not the best possible one.

SUMMARY OF THE INVENTION

According to the basic idea of the invention disclosed in this application, a curved path is arranged for the radiation source of the imaging apparatus in the vertical direction with respect to the object to be imaged, e.g. by attaching the radiation source substantially to one end of a curved suspension arm and by attaching the other end of the arm to the imaging apparatus either stationarily or so that the arm can be moved in the direction of its longitudinal axis, in which case the curved movement can be produced either by moving the radiation source along a guide track in the arm, for example, or by moving the arm in the direction of its longitudinal axis along a stationary supporting structure in the vertical direction with respect to the object to be imaged. Naturally there are numerous ways of producing such a curved movement. For example, the suspension arm does not need to be curved, but the radiation source can be moved e.g. by moving a pivoted suspension arm programmatically. The radiation source may also be placed inside a casing or the like so that the curvature of the vertical movement cannot be detected from outside.

The counter-movement of the curved movement in the vertical direction of the radiation source is implemented according to the invention by moving the radiation detector substantially linearly on the opposite side of the object to be imaged with respect to the radiation source. In that case the distance of the detector from the object to be imaged changes slightly during the imaging session, which causes a theoretical change in magnification. This error, however, lacks practical relevance in the case of the layer thicknesses that are normally imaged with the solutions according to the invention.

According to the invention it is also particularly preferable to keep the detector constantly parallel with one shear plane that is to be imaged from the object in a manner known per se. In the direction of the vertical movement this parallelism is achieved automatically when the inventive method is used. If this mode known per se were to be implemented in solutions known from Finnish Patent 88671, for example, the detector would have to be provided with a degree of freedom for moving in the direction of the axis between the imaging means in order to provide the curved path of the detector in the vertical direction.

According to the invention, the vertical movements of the radiation source and the detector can be synchronized by connecting them mechanically with each other. Alternatively, their vertical movements can be implemented by the control of separate actuators.

The embodiments of the invention combine the ideas of utilizing structures that already exist in several imaging devices for producing a tomographic effect and the object of producing a vertical movement without having to move large masses, which imposes limitations on tomographic imaging. According to some preferred embodiments of the invention, the vertical path of the imaging means can implemented using the moving means of the imaging means that are already included in devices of this kind for some other reasons. Thus the apparatuses will be relatively simple in structure as well as economical, since the existing solutions can be utilized as such or with minor structural or programmatical changes for complex motion tomographic imaging.

Many preferred embodiments of the invention also provide a better resolution than the prior art solutions.

More precisely, characteristic features of the invention are described in the characterizing parts of the appended independent claims.

In the following some preferred embodiments of the invention will be described by examples with reference to the accompanying drawings.

DETAILED DESCRIPTION OF THE DRAWINGS

Figure 1:
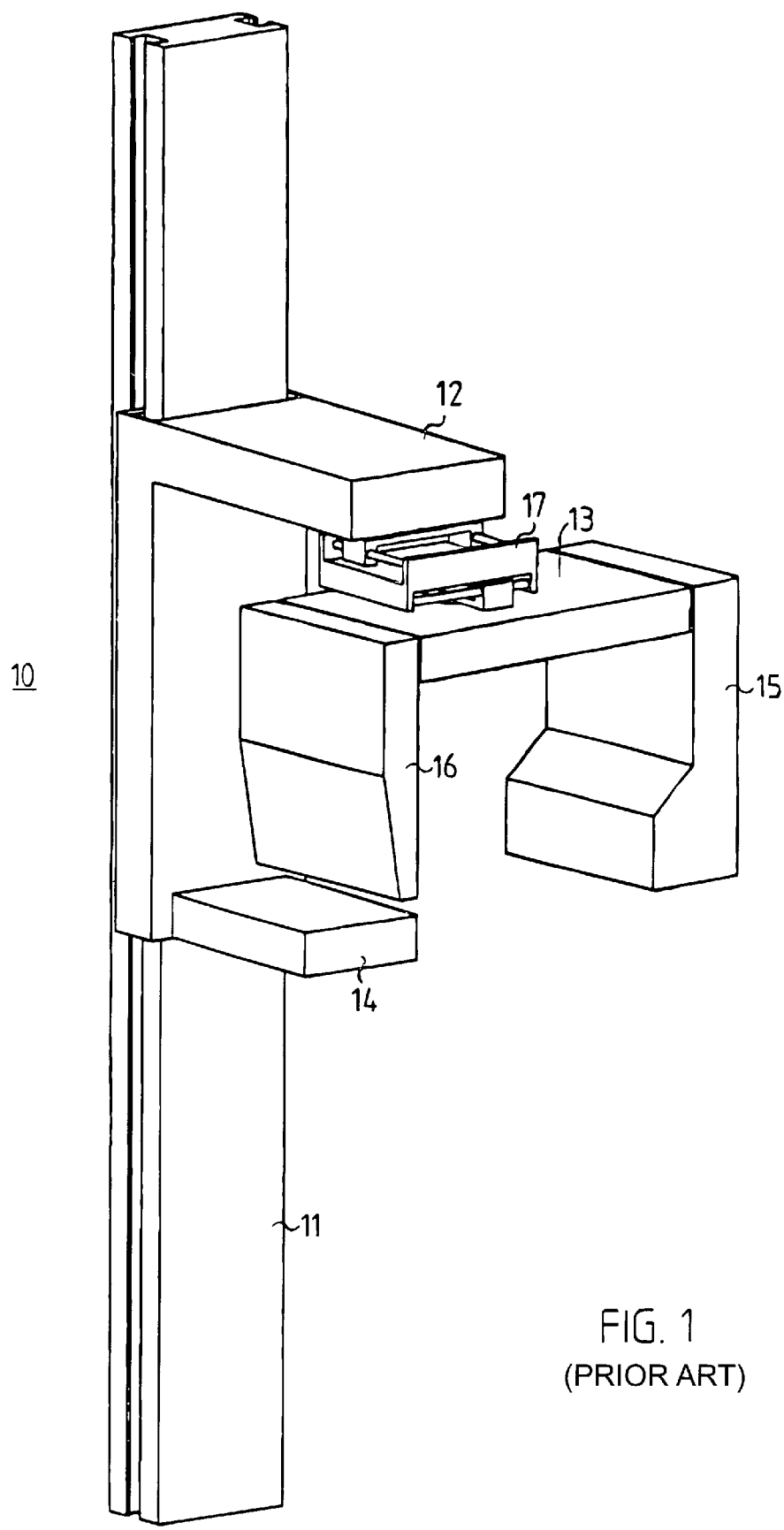
FIG. 1 illustrates a typical prior art apparatus used for imaging the teeth and the cranial area.
Figure 2:
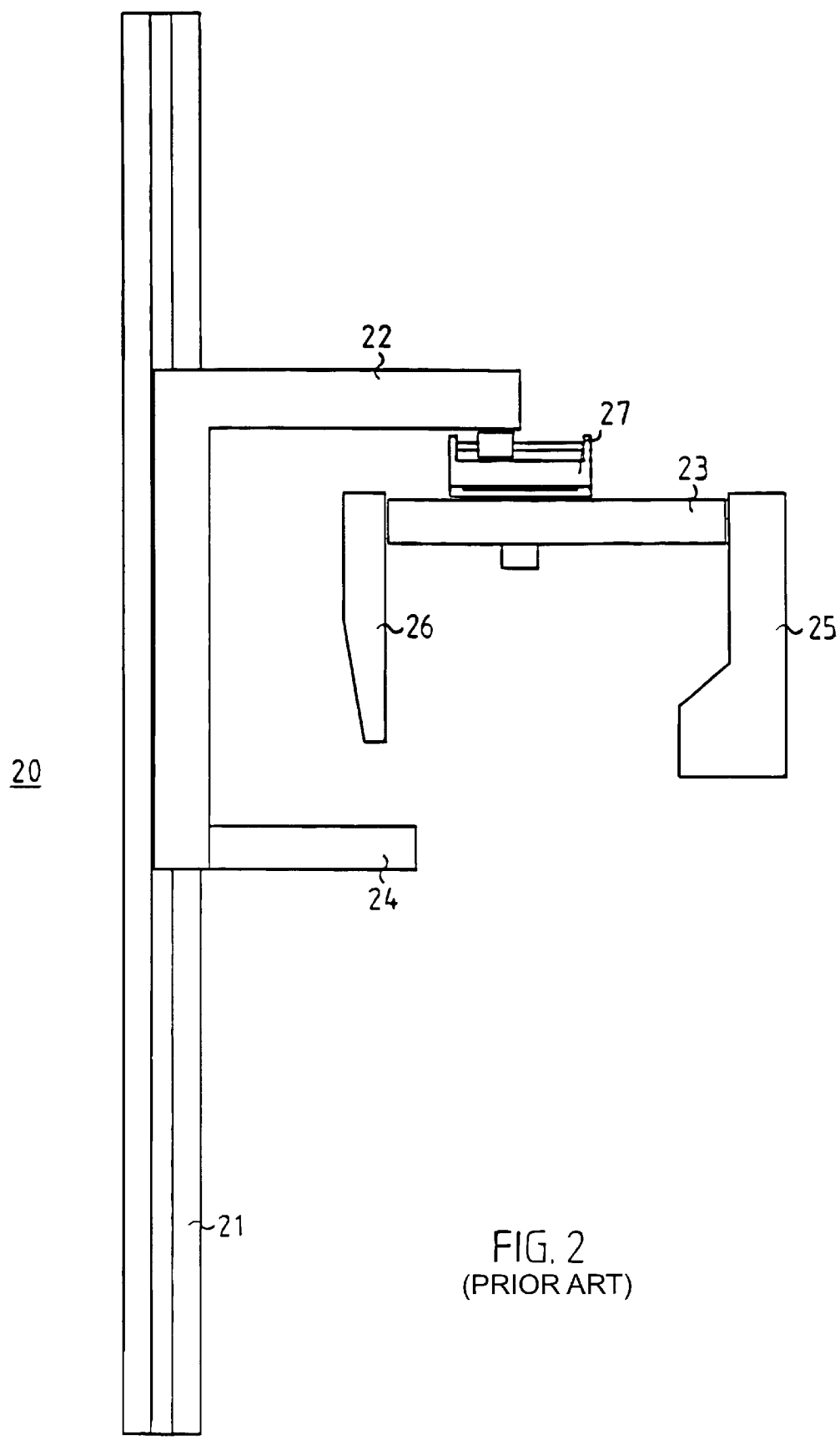
FIG. 2 is a side view of the apparatus according to FIG. 1.

FIGS. 1 and 2 illustrate a typical prior art apparatus (10, 20) for imaging the teeth and the cranial area, which according to the invention can also be used for complex motion tomographic imaging with relatively small changes.

The apparatus (10, 20) consists of a first frame part (11, 21), a second frame part (12, 22) and a third frame part (13, 23). The first frame part (11, 21) may be attached to the floor or wall, in which case it comprises means for altering the height of the second frame part (12, 22). Alternatively, the second frame part (12, 22) may be fixed to the first frame part (11, 21), in which case the first frame part (11, 21) comprises means for adjusting its length (e.g. a telescopic structure). The third frame part (13, 23) functions as a suspension arm of the radiation source (15, 25) and the detector (16, 26), i.e. the imaging means, which are attached to the opposite ends of the suspension arm. The third frame part is attached to the second frame part using the fixing and moving means (17, 27). The means for positioning the object to be imaged in the right place may be arranged in a fourth frame part (14, 24), which may also comprise the control panel of the apparatus.

For the sake of clarity it should be noted that in this application the entity formed by the second and third frame parts is also called "imaging equipment", the radiation source and the radiation detector "imaging means" and the third frame part "suspension arm".

In some prior art devices the fixing and moving means (17, 27) which connect the second frame part (12, 22) and the third frame part (13, 23), i.e. the suspension arm of the imaging means, allow the suspension arm (23) to rotate and move horizontally in the x and y directions. The apparatus often comprises a control system for the movements of the suspension arm (13, 23), which may be implemented e.g. by means of computer-controlled electric motors and guide tracks provided in the fixing and moving means (17, 27) of the suspension arm. The structures that move the suspension arm can be implemented in various ways. Usually in apparatuses of this kind the common object is to allow the suspension arm to rotate around its fixing point and to move this fixing point in the desired manner with respect to the object to be imaged in the horizontal plane. In addition, if a film or the like is used as the detector (16, 26), the apparatuses often also include means for moving the film in the horizontal direction.

Figure 3:
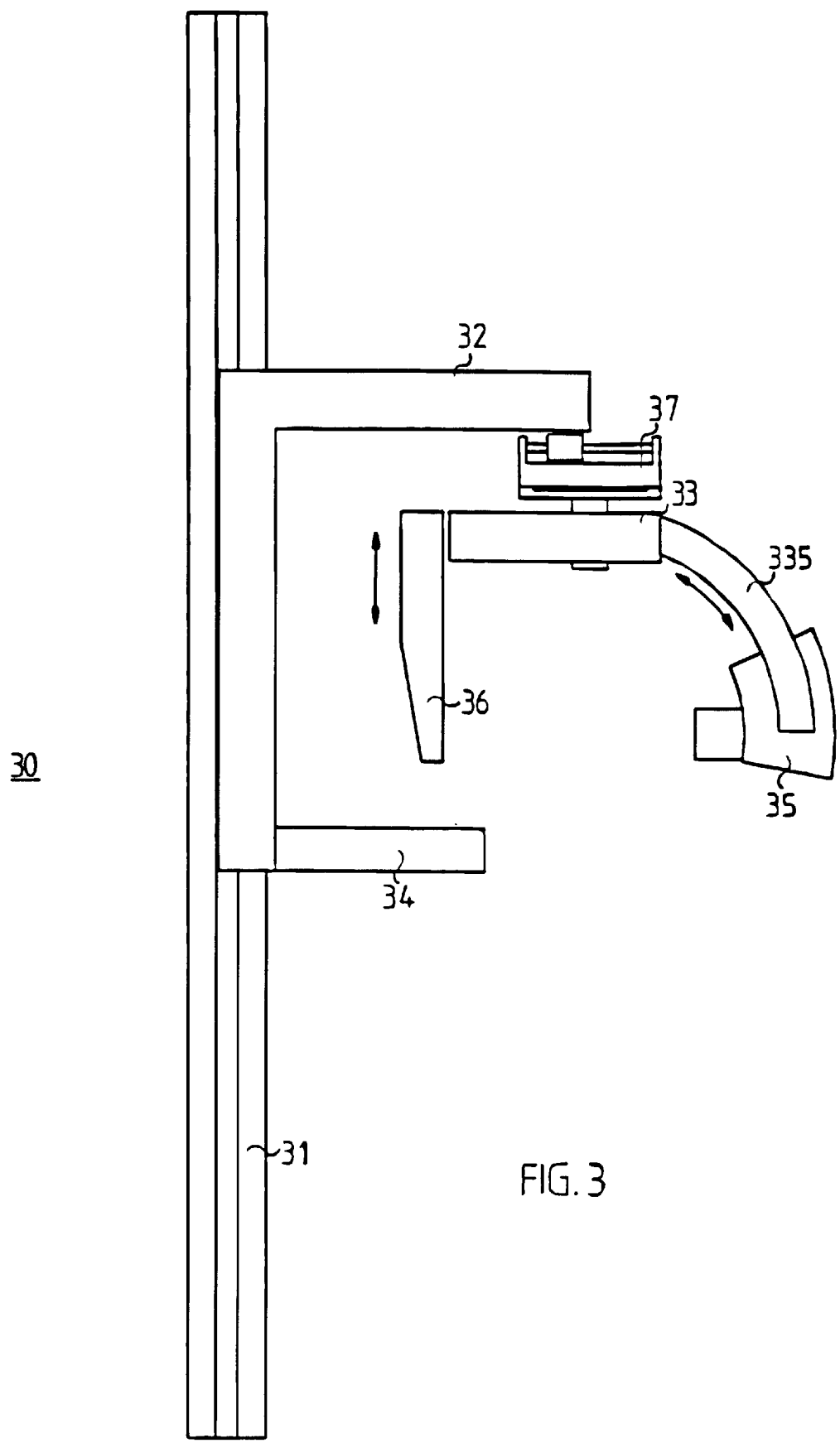
FIG. 3 is a side view of an apparatus according to the invention.

FIG. 3 illustrates one inventive way of modifying a prior art apparatus so that it can also be used for complex motion tomographic imaging. The parts of the apparatus illustrated in FIG. 3 correspond to the parts of the apparatuses illustrated in FIGS. 1 and 2, except that the suspension arm (33) is provided with a separate suspension arm (335) for the radiation source (35). In the solution of FIG. 3 this arm (335) is curved so that it can be moved along the supporting structure arranged to the arm (33) e.g. by means of the fixing and moving means (not shown) attached to the suspension arm (33) to move the radiation source (35) along the curved path of the arm in the vertical direction with respect to the object to be imaged. The fixing and moving means of the detector (36) that are not shown allow to move the detector at the end of the suspension arm (33) (at least) in linear and vertical direction with respect to the object to be imaged.

Figure 4:
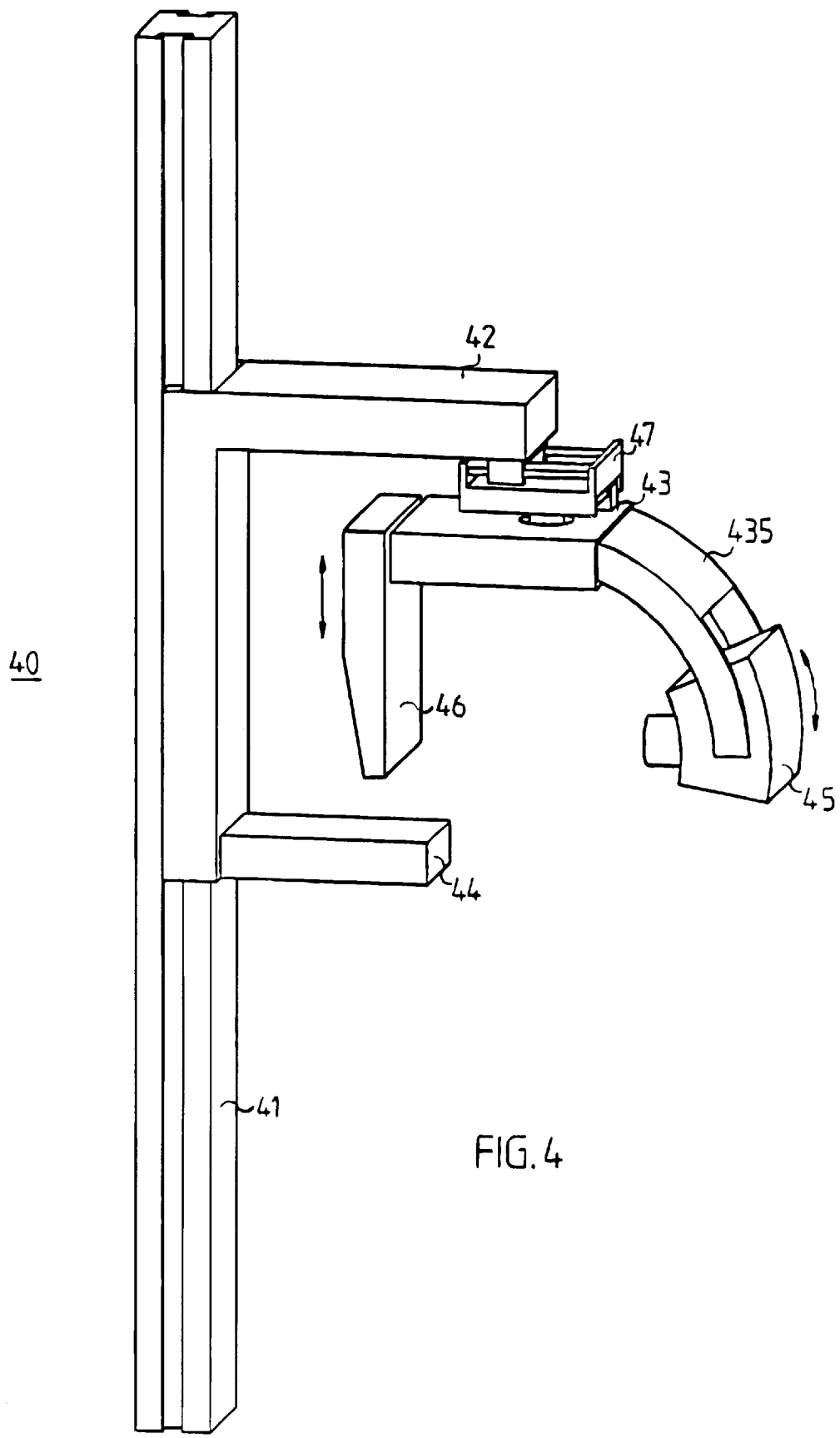
FIG. 4 illustrates one way of attaching a radiation source to the apparatus according to the invention.

According to a preferred embodiment of the invention, the curved suspension arm (435) of the radiation source (45) is mounted immovably to the suspension arm and the radiation source (45) is moved along the curved suspension arm (435) by the fixing and moving means that are not shown (FIG. 4). The radiation source (45) can be moved either simply in the direction of the tangent of the arm (435) or in the desired manner, deviating slightly from this main direction of movement.

It is also possible to arrange the movement of the suspension arm (335, 345) to move the radiation source in the vertical direction (description of FIG. 3 above) and to arrange the fixing and moving means of the radiation source (35, 45) not shown in FIG. 4 so that they allow the radiation source (35, 45) to move in the horizontal direction with respect to the object to be imaged. Such a structure, which may comprise an independent actuator for the detector (36, 46) for producing the horizontal movement with respect to the object to be imaged, offers various alternatives for producing different complex motion tomographic images.

According to the invention, it is preferable to keep the detector (36, 46) parallel with one shear plane (i.e., a cross sectional plane through the object) which is to be imaged during the whole imaging session. To be able to produce images also in the horizontal direction, in which the movement is often curved, the detector (36, 46) has to be attached to the suspension arm (33, 43) using e.g. suitable pivoting known per se in the field (attachment is not shown in the figures).

A way of implementing imaging according to the invention, which is preferable in several respects, comprises moving of the radiation source in the vertical direction with respect to the object to be imaged along a substantially curved path so that the object to be imaged is substantially in the centre of this path. Thus e.g. controlling of imaging in such complex motion imaging comprising several motions may be simpler to implement. An advantage of this is that the direction of the beam collimation does not need to be changed during radiation since the beam is automatically directed towards the object to be imaged.

The invention is best suited for imaging where the beam is of the same size as the object to be imaged, but naturally it is also applicable to narrow beam tomography. In that case, however, the imaging process is relatively slow, which imposes practical limitations on this application of the invention.

In some imaging modes it may be preferable to implement the vertical path of the detector so that it deviates slightly from the purely linear main direction of movement according to the invention. In one preferred embodiment of the invention it may also be advantageous to allow slight movement or deviation from the requirement of keeping the detector parallel with the shear plane to be imaged.

The tomographic movement is usually implemented so that it is continuous, but in some cases it may be necessary to stop the movement and/or radiation momentarily for purely technical reasons.

The above examples illustrate applications of the invention mainly by means of devices known from odontological X-ray photography. Even though the invention is particularly suitable for developing solutions known from odontological X-ray photography of the cranial area, its applicability is not limited only to the embodiments described by the examples. The following claims define the scope of the invention, and several details of the invention may vary within the inventive concept disclosed in the claims.

What is claimed is:

1. A method of producing complex motion or spiral tomography images in which an object to be imaged is held in place and in which a detector, located substantially on an opposite side of the object to be imaged, receives radiation of a beam from a radiation source whereby a tomographic effect is produced by moving the radiation source and detector in the direction of a first and a second axis with respect to the object to be imaged, the first axis being substantially horizontal to the object to be imaged, and the second axis, being substantially vertical to the object to be imaged, wherein movement in the direction of the second axis is implemented by moving the radiation source along a substantially curved path, and a counter-movement of the detector with respect to vertical movement of the radiation source along said curved path is implemented by moving the detector substantially linearly on the opposite side of the object to be imaged.

2. A method according to claim 1, wherein the detector is held constantly substantially parallel with one cross sectional plane to be imaged.

3. A method according to claim 1, wherein said curved path of the radiation source is implemented by attaching the radiation source to a curved suspension arm and by moving the radiation source along the curved suspension arm.

4. A method according to claim 1, wherein said curved path of the radiation source is implemented by attaching the radiation source to a curved suspension arm and by moving the suspension arm along a supporting structure, which is stationary, in the direction of vertical movement with respect to the object to be imaged.

5. A method according to claim 1, wherein said curved path of the radiation source is implemented by controlling a pivotable and motorized suspension structure of the radiation source.

6. A method according to claim 1, wherein the movement and the counter-movement of the radiation source and detector in the direction of the second axis are controlled by separate actuators.

7. A method according to claim 1, wherein the movement and the counter-movement of the radiation source and detector in the direction of the second axis are synchronized mechanically.

8. A method according to claim 1, wherein, in the vertical direction with respect to the object to be imaged, the radiation source is moved along a substantially curved path with respect to which the object to be imaged is substantially in the center of the curve during an entire imaging session.

9. A method according to claim 1, wherein before the beam is guided onto the object to be imaged, a width of the beam is defined so that the beam is narrower than the object to be imaged.

10. A method according to claim 1, wherein the electromagnetic radiation is X-radiation.

11. Apparatus for producing complex motion and spiral tomography images using radiation during tomographic movement, the apparatus comprising a radiation source for generating an electromagnetic beam, a radiation detector, first means for moving the radiation source and the detector in a controlled manner, and second means for placing an object to be imaged substantially between the radiation source and the detector, said first means allowing controlled movement of the radiation source and the detector substantially on opposite sides of the object to be imaged in the direction of a first and a second axis, the first axis being substantially horizontal to the object to be imaged, and the second axis being substantially vertical to the object to be imaged, said first means including means for moving the radiation source along a substantially curved path in the direction of the second axis, and means for implementing a counter-movement of the detector with respect to vertical movement of said radiation source such that the detector moves along a substantially linear path on the opposite side of the object to be imaged.

12. Apparatus according to claim 11, further comprising means for keeping the detector constantly substantially parallel with one cross sectional plane to be imaged.

13. Apparatus according to claim 11, wherein the means for moving the radiation source along the curved path comprise a curved suspension arm and fixing and moving means for moving the radiation source along said curved suspension arm.

14. Apparatus according to claim 13, wherein the radiation source and/or the detector are provided with fixing and moving means for moving the radiation source and/or the detector independently of the movement of the curved suspension arm in the horizontal direction with respect to the object to be imaged.

15. Apparatus according to claim 11, wherein the means for moving the radiation source along the curved path comprise a curved suspension arm, the radiation source being attached substantially to one end of said curved suspension arm, and means for moving said curved suspension arm along a stationary support structure in the vertical direction with respect to the object to be imaged.

16. Apparatus according to claim 11, wherein the means for moving the radiation source along a curved path comprise a control system for a pivotable and motorized suspension structure of the radiation source.

17. Apparatus according to claim 11, wherein the means for producing the movement of the radiation source and counter-movement of the detector in the vertical direction are controlled by separate actuators.

18. Apparatus according to claim 11, wherein the means for producing the movement of the radiation source and counter-movement of the detector in the vertical direction are connected with each other by mechanical synchronization.

19. Apparatus according to claim 11, wherein said first and second means locate the object to be imaged substantially in the center of the substantially curved path of movement of the radiation source in the vertical direction with respect to the object to be imaged during an entire imaging session.

20. Apparatus according to claim 11, further comprising means for collimating the electromagnetic beam so that the electromagnetic beam is narrower than the object to be imaged before the electromagnetic beam is guided onto the object to be imaged.

21. Apparatus according to claim 11, wherein the radiation source comprises an x-ray tube.

22. Apparatus according to claim 11, further comprising a first frame part for attaching the apparatus to a floor, wall or another supporting structure, a second frame part which can be moved in the vertical direction with respect to the first frame part, the radiation source for producing an electromagnetic beam and the radiation detector being connected to the second frame part by a third frame part, to which the radiation source and the radiation detector are fixed.

23. Apparatus according to claim 22, wherein the means for producing the movement and counter-movement of the radiation source and detector in the direction of the horizontal axis with respect to the object to be imaged, comprise a structure in which the radiation source and detector are attached substantially to opposite ends of the third frame part, the structure comprising means for rotating the third frame part with respect to the object to be imaged.

24. Apparatus according to claim 23, wherein said means for rotating the third frame part includes means for moving a fixing point and/or center of rotation of the third frame part in the horizontal plane.

* * * * *